(12) United States Patent
Taira

(10) Patent No.: US 12,405,105 B2
(45) Date of Patent: Sep. 2, 2025

(54) METHOD FOR OPERATING AN OPTICAL TOMOGRAPHIC IMAGING APPARATUS

(71) Applicant: GENESIS MEDTECH JAPAN CO., LTD., Tokyo (JP)

(72) Inventor: Kenji Taira, Musashino (JP)

(73) Assignee: GENESIS MEDTECH JAPAN CO., LTD., Tokyo (JP)

(*) Notice: Subject to any disclaimer, the term of this patent is extended or adjusted under 35 U.S.C. 154(b) by 181 days.

(21) Appl. No.: 18/111,130

(22) Filed: Feb. 17, 2023

(65) Prior Publication Data

US 2023/0213328 A1 Jul. 6, 2023

Related U.S. Application Data

(63) Continuation of application No. PCT/JP2021/029914, filed on Aug. 16, 2021.

(30) Foreign Application Priority Data

Aug. 19, 2020 (WO) .................. PCT/JP2020/031214

(51) Int. Cl.
*G01B 9/02091* (2022.01)
*A61B 5/00* (2006.01)
(Continued)

(52) U.S. Cl.
CPC ........ *G01B 9/02091* (2013.01); *A61B 5/0066* (2013.01); *G01B 9/0203* (2013.01); *G01B 9/02084* (2013.01)

(58) Field of Classification Search
CPC .............. G01B 9/02091; G01B 9/0203; G01B 9/02084; G01B 9/02004; A61B 5/0066; A61B 5/6852; A61B 1/00
See application file for complete search history.

(56) References Cited

U.S. PATENT DOCUMENTS

2012/0162660 A1 6/2012 Kemp
2012/0250029 A1* 10/2012 Yoshida ............. G01B 9/02044
356/497
(Continued)

FOREIGN PATENT DOCUMENTS

JP 2018-164495 A 9/2016
WO WO 2010/137373 A1 12/2010
WO WO 2018/047773 A1 3/2016

OTHER PUBLICATIONS

Extended European Search Report for European Application No. 21858272.4, dated Jun. 11, 2024.
(Continued)

*Primary Examiner* — Michael P LaPage
(74) *Attorney, Agent, or Firm* — Birch, Stewart, Kolasch & Birch, LLP

(57) ABSTRACT

A method for operating an optical tomographic imaging apparatus according to the present invention includes: an initial setting step of setting initial positions of a reference mirror and a distal end of an optical part; an imaging step of imaging a biological tubular element after the initial setting step; a reference mirror adjustment step of, after the imaging step, moving the reference mirror to enlarge the image portion of the reflected light from the biological tubular element and the image portion of the reflected light from the tube while reducing an image portion of an artifact caused by reflected light from the optical part, and adjusting the image portion of the artifact to an inside of the image portion of the reflected light from the tube; a magnification adjustment step of, after the reference mirror adjustment step, resetting the image portion of the reflected light from the biological tubular element and the image portion of the reflected light from the tube to a state before the enlargement; and a display step of, after the magnification adjustment step, causing an image display unit to display the (Continued)

image portion of the reflected light from the biological tubular element and the image portion of the reflected light from the tube reset to the state before enlargement.

10 Claims, 5 Drawing Sheets

(51) Int. Cl.
  *G01B 9/02* (2022.01)
  *G01B 9/02015* (2022.01)

(56) References Cited

U.S. PATENT DOCUMENTS

| 2015/0099984 A1* | 4/2015 | Kankaria | A61B 5/0066 600/478 |
| 2017/0224286 A1 | 8/2017 | Sakamoto | |
| 2018/0372477 A1 | 12/2018 | Elmaanaqui | |
| 2019/0223699 A1* | 7/2019 | Wu | A61B 1/00188 |
| 2019/0374109 A1* | 12/2019 | Wu | G06T 11/008 |
| 2021/0174125 A1* | 6/2021 | Zhang | G06T 7/12 |

OTHER PUBLICATIONS

English translation of International Preliminary Report on Patentability and Written Opinion of the International Searching Authority for International Application No. PCT/JP2021/029914, dated Mar. 2, 2023.
English translation of International Preliminary Report on Patentability for International Application No. PCT/JP2020/031214, dated Feb. 23, 2023.
English translation of International Search Report for International Application No. PCT/JP2020/031214. dated Oct. 13, 2020.
English translation of International Search Report for International Application No. PCT/JP2021/029914, dated Oct. 19, 2021.

* cited by examiner

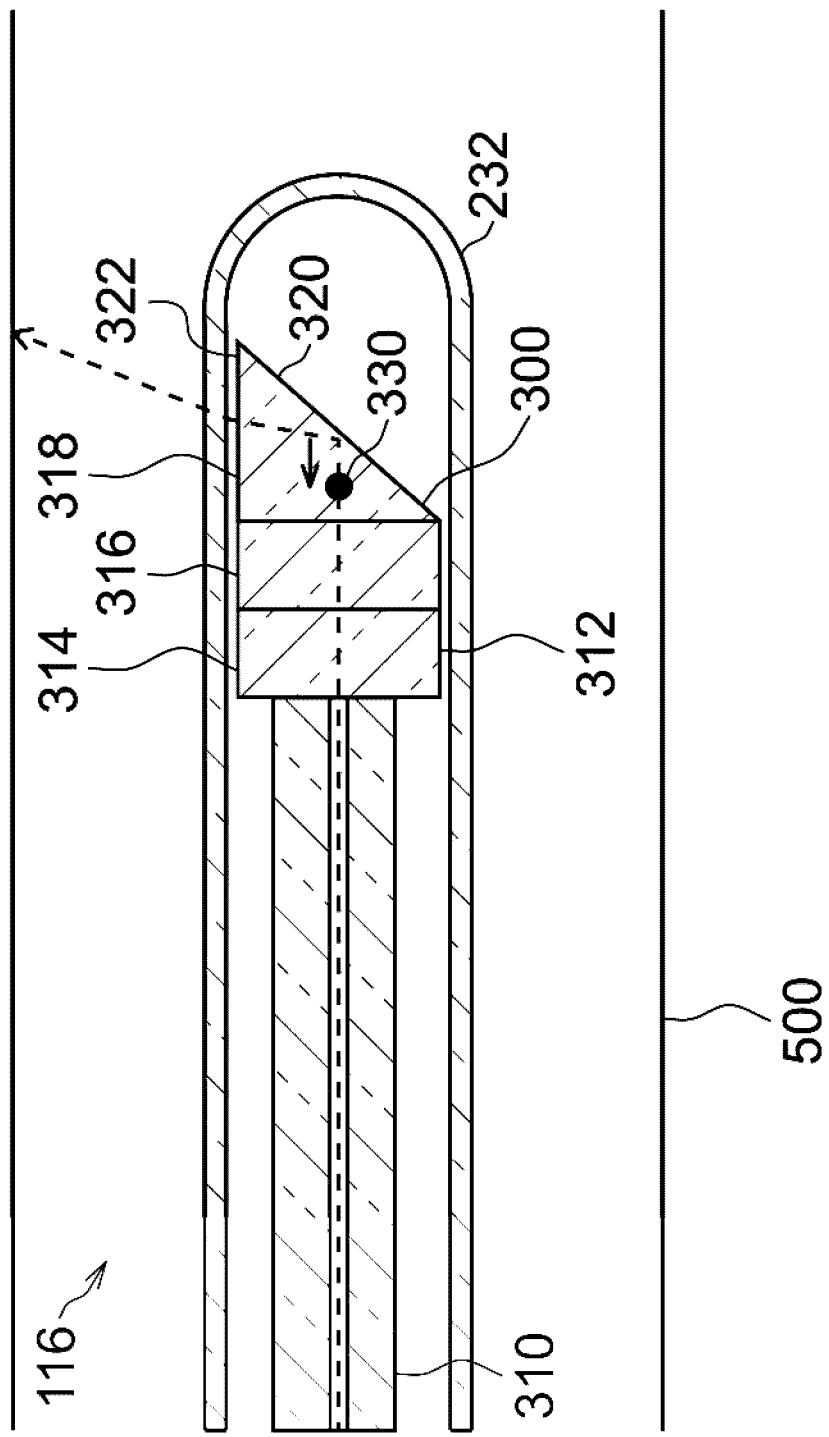

METHOD FOR OPERATING AN OPTICAL TOMOGRAPHIC IMAGING APPARATUS

CROSS-REFERENCE TO RELATED APPLICATIONS

This is a continuation application of International Application No. PCT/JP2021/029914, with an International filing date of Aug. 16, 2021, which claims priority of International Application No. PCT/JP2020/031214 filed on Aug. 19, 2020, the entire content of which is hereby incorporated by reference.

TECHNICAL FIELD

The present invention relates to a method for operating an optical tomographic imaging apparatus.

BACKGROUND ART

Patent Document 1 (WO 2016/047773 A1) discloses a Swept Source Optical Coherence Tomography (SS-OCT) as a tomographic imaging system for imaging tomographic images of biological tissues such as various biological tubular elements including, for example, a gastrointestinal tract, a pancreaticobiliary duct, a fallopian tube, a urethra, a trachea, a blood vessel, and a lymph duct. This SS-OCT includes a wavelength swept light source that sequentially switches a wavelength and emits light, a reference mirror, and an optical probe that irradiates a biological tubular element with the light emitted from the wavelength swept light source. At a time of imaging, the light emitted from the wavelength swept light source is radiated toward the reference mirror and the optical probe in a state where the optical probe is inserted into a blood vessel to obtain interference light of reference mirror reflected light reflected by the reference mirror, and blood vessel reflected light reflected by the blood vessel through the optical probe. By detecting this interference light and performing Fourier transform, it is possible to obtain a tomographic image in a radial direction of the blood vessel.

However, a plurality of optical parts are incorporated in the optical probe and optically coupled, light is reflected or scattered at boundary surfaces (e.g., light incident surfaces and light emission surfaces of the optical parts) of these optical parts, and this reflected light or scattered light may appear as an artifact in a tomographic image. There is a risk that the artifact not only lowers clarity of the image, but also make it difficult to perform correct diagnosis when the artifact overlaps a tissue image.

SUMMARY OF THE INVENTION

Therefore, the present invention provides a method for preventing an artifact from overlapping an image of a biological tubular element in a tomographic image.

Means for Solving the Problems

In order to achieve this object, a method for operating an optical tomographic imaging apparatus is provided, the optical tomographic imaging apparatus comprising:
  a light source;
  a splitter that splits light emitted from the light source into first light and second light;
  a translucent tube that is inserted into a biological tubular element;
  an imaging unit that includes an optical fiber having a proximal end optically coupled to the splitter, and an optical part provided at a distal end of the optical fiber, and that emits the first light guided by the optical fiber from the optical part toward an inner wall of the biological tubular element through the tube, and obtain reflected light of the first light returning from the biological tubular element via the tube, from the optical part through the optical fiber;
  an optical distance adjustment unit that includes a movable reference mirror, and is capable of obtaining reference light by reflecting the second light on the reference mirror, and adjusting an optical distance of the second light by moving the reference mirror;
  an interference unit that causes the reflected light and the reference light to interfere with each other, and obtains interference light;
  a detection unit that detects the interference light of the reflected light and the reference light;
  a conversion unit that converts the interference light detected by the detection unit into an electrical signal;
  a Fourier transform unit that performs Fourier transform on the electrical signal obtained by the conversion unit, and obtains a light intensity distribution with respect to an optical distance difference between an optical distance of the reflected light and an optical distance of the reference light;
  an image processing unit that deletes an image portion of an artifact caused by the optical part from an image imaged by the image imaging unit, and obtains an image without the artifact;
  an image display unit; and
  a control unit that controls the imaging unit, the optical distance adjustment unit, the image processing unit, and the image display unit,
  the method comprising executing, by the control unit:
  (a) an initial setting step of controlling the optical distance adjustment unit to set an optical distance of the reference light substantially equally to an optical distance of the reflected light, the optical distance of the reference light being an optical distance that light emitted from the light source travels until reaching the detection unit after being reflected by the reference mirror, and the optical distance of the reflected light being an optical distance obtained by adding a first optical distance from the light source to a distal end of the optical part and a second optical distance from the distal end of the optical part to the detection unit;
  (b) an imaging step of, after the initial setting step, operating the imaging unit to image the biological tubular element;
  (c) a reference mirror adjustment step of, after the imaging step, controlling the optical distance adjustment unit to move the reference mirror to make the optical distance of the reference light shorter than the optical distance of the reflected light, thereby enlarge the image portion of reflected light from the biological tubular element and the image portion of reflected light from the tube while reducing an image portion of an artifact caused by the reflected light from the optical part, and fitting the image portion of the artifact to an inside of the image portion of the reflected light from the tube;
  (d) a magnification adjustment step of, after the reference mirror adjustment step, controlling the image processing unit to reset the image portion of the reflected light from the biological tubular element and the image portion of the reflected light from the tube to a state before the enlargement; and
  (e) a display step of, after the magnification adjustment step, causing the image display unit to display the image portion of the reflected light from the biological tubular element and the image portion of the reflected light from the tube reset to the state before the enlargement.

BRIEF DESCRIPTION OF THE DRAWINGS

The present invention will become more fully understood from the detailed description given hereinbelow and the accompanying drawings which are given by way of illustration only, and thus are not limitative of the present invention, and wherein:

FIG. 2 is a cross-sectional view of an optical probe included in the optical tomographic imaging device illustrated in FIG. 1.

EMBODIMENTS OF THE INVENTION

Hereinafter, embodiments of an optical tomographic imaging method according to the present invention and an optical tomographic imaging device that uses this method will be described with reference to the accompanying drawings.

[Optical Tomographic Imaging Device]

Figure 1:
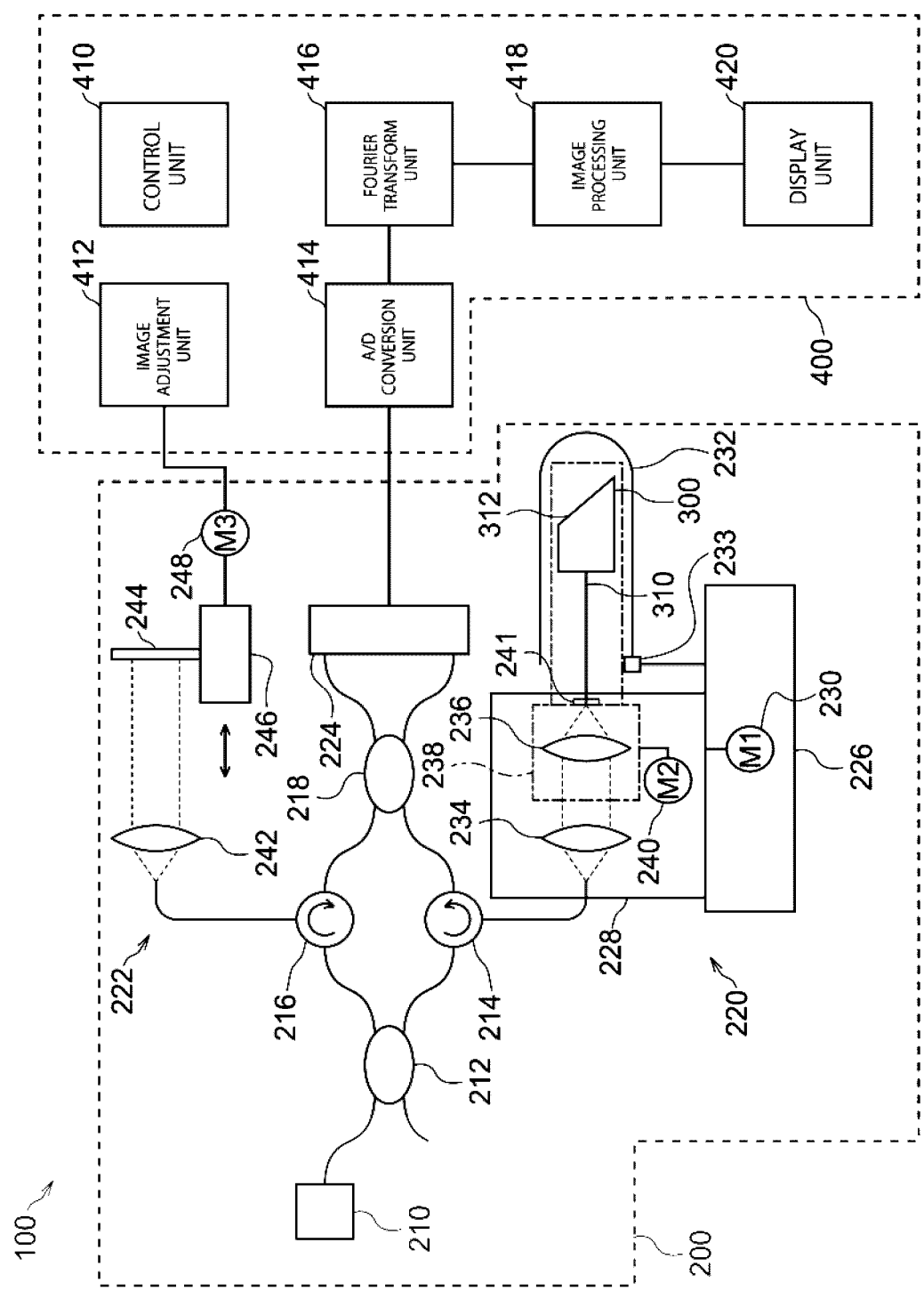
FIG. 1 is a view illustrating a schematic configuration of an optical tomographic imaging device according to an embodiment of the present invention.

FIG. 1 illustrates an outline of a Swept Source Optical Tomograph (SS-OCT) device according to the embodiment.

An SS-OCT 100 includes an optical unit 200 and a signal processing unit 400.

[Optical Unit]

The optical unit 200 includes a plurality of optical elements. The plurality of optical elements include a wavelength swept light source 210, a first optical coupler 212, a first optical circulator 214, a second optical circulator 216, a second optical coupler 218, a biological tubular element imaging unit 220, an optical distance adjustment unit 222, and a detection unit 224. The relevant elements of these optical elements are optically coupled by light transmission elements such as optical fibers as described below.

[Wavelength Swept Light Source]

The wavelength swept light source 210 outputs light necessary for imaging a cross-section of a biological tubular element. The wavelength swept light source 210 is configured to be able to cyclically change a wavelength of light to be output, and sweep a wavelength from 1260 nm to 1360 nm at, for example, 100 kHz in frequency.

[First Optical Coupler]

The first optical coupler (splitter) 212 is a portion that is optically coupled by heating and fusing part of two optical fibers disposed in parallel. One of the two optical fibers optically couples the first optical coupler 212 and the first optical circulator 214, and the other optical fiber optically couples the wavelength swept light source 210 and the second optical circulator 216 with the first optical coupler 212 interposed therebetween. Therefore, light output from the wavelength swept light source 210 is split into two light beams by the first optical coupler 212, the one split light beam is sent to the first optical circulator 214, and the other split light beam is sent to the second optical circulator 216.

[First Optical Circulator]

The first optical circulator 214 is a 3-port optical circulator, includes a first port coupled to the first optical coupler 212, a second port coupled to the second optical coupler 218, and a third port coupled to the biological tubular element imaging unit 220, and is configured to send to the biological tubular element imaging unit 220 the light sent from the wavelength swept light source 210 to the first optical circulator 214 through the first optical coupler 212, and send to the second optical coupler 218 light returned from the biological tubular element imaging unit 220.

[Second Optical Circulator]

The second optical circulator 216 is a 3-port optical circulator, includes a first port coupled to the first optical coupler 212, a second port coupled to the second optical coupler 218, and a third port coupled to the optical distance adjustment unit 222, and is configured to send to the optical distance adjustment unit 222 the light sent from the wavelength swept light source 210 to the second optical circulator 216 through the first optical coupler 212, and send to the second optical coupler 218 light returned from the optical distance adjustment unit 222.

[Second Optical Coupler]

At a portion at which an optical fiber having one end (proximal end) connected to the first optical circulator 214 and a middle of an optical fiber having one end (proximal end) connected to the second optical circulator 216 are heated and fused, and optically coupled, the second optical coupler 218 (interference unit) overlaps light (reflected light) sent from the biological tubular element imaging unit 220 to the second optical coupler 218 through the first optical circulator 214, and light (reference light) sent from the optical distance adjustment unit 222 to the second optical coupler 218 through the second optical circulator 216 to obtain interference light.

[Biological Tubular Element Imaging Unit]

The biological tubular element imaging unit 220 includes a base 226, and a linear motion unit (pull-back unit) 229 that linearly moves in a predetermined direction (a left-right direction in FIG. 1) with respect to the base 226. The linear motion unit 228 is coupled to a linear motion motor 230 provided to the base 226, and is configured to move forward or backward in the predetermined direction based on driving of the linear motion motor 230. To the base 226, a proximal end part of a hollow cylindrical flexible tube (referred to as a sheath below) 232 made of a translucent resin is detachably fixed by a retainer 233. As illustrated, the sheath 232 includes an opened proximal end, and a closed distal end.

The linear motion unit 228 is provided with a proximal end side collimation lens 234 and a distal end side collimation lens 236. The proximal end side collimation lens 234 and the distal end side collimation lens 236 are aligned at a fixed interval on one optical axis, and light having passed through the proximal end side collimation lens 234 is transmitted on the optical axis of the distal end side collimation lens 236.

The proximal end side collimation lens 234 is fixed to the linear motion unit 228, and is optically coupled to the first optical circulator 214 with the optical fiber interposed therebetween.

The distal end side collimation lens 236 is supported by a rotation unit 233 provided to the linear motion unit 228. In a state where a fixed distance between the proximal end side collimation lens 234 and the distal end side collimation lens 236 is kept, the rotation unit 238 is supported by the linear motion unit 229 rotatably about the optical axes of the proximal end side collimation lens 234 and the distal end side collimation lens 236.

The rotation unit 238 is drivingly coupled to a rotation motor 240 fixed to the linear motion unit 228 with a rotation transmission mechanism (not illustrated) interposed therebetween and including, for example, a gear and a toothed belt.

An optical probe 300 is detachably coupled to the rotation unit 234. The optical probe 300 includes an optical fiber 310 and an optical part 312. The optical part 312 is coupled to a distal end of the optical fiber 310. A proximal end of the optical fiber 310 is detachably coupled to the rotation unit 238 with a connector 241 interposed therebetween, and the optical fiber 310 is configured to rotate together with rotation of the rotation unit 238 such that light condensed by the distal end side collimation lens 236 is incident on a core of the optical fiber 310 from the proximal end of the optical fiber 310.

The optical part 312 coupled to the distal end of the optical fiber 310 includes a plurality of optical elements. In the embodiment, the plurality of optical elements include a glass rod (first lens) 314, a grin lens (second lens) 316, and, in addition, a prism 318 that is a deflection part (see FIG. 2). The glass rod 314, the grin lens 316, and the prism 318 are disposed in this order from the proximal end side toward the distal end side, and the adjacent optical elements are mechanically and optically coupled to each other by fusion or an adhesive of a translucent resin.

The glass rod 314 that has a cylindrical shape and the grin lens 316 that is a cylindrical lens are installed coaxially with respect to an extension line (optical axis) of the optical axis of the optical fiber 310. A substantially right angle prism having a triangular prism shape is used for the prism 314 that is a deflection part, and one side (surface) of two sides (sides other than an oblique side) sandwiching the substantially right angle is coupled to a distal end surface of the grin lens 316. Therefore, light emitted from the distal end of the optical fiber 310 enters the prism 318 from one side (surface) on the proximal end side through the glass rod 314 and the grin lens 316. The light having entered the prism 318 is reflected by an inclined surface (oblique side), then travels in a direction orthogonal to the optical axis, and is emitted in a radial direction from the other side (surface) on the distal end side. Conversely, light having entered the prism 318 from the other side (surface) on the distal end side is reflected by the inclined surface (oblique side), then sequentially passes through the grin lens 316 and the glass rod 314 through one side (surface) on the proximal end side, and is incident on the optical fiber 310.

In order to suppress as much as possible the light reflected by end surfaces of the optical fiber 310 and the optical part 312 and returned to the optical fiber 310 among the light sent through the optical fiber 310, a distal end surface of the optical fiber 310, proximal end side end surfaces and distal end side end surfaces of the glass rod 314 and the grin lens 316, and a proximal end surface of the prism 318 are preferably inclined slightly with respect to a plane perpendicular to the optical axis (e.g., approximately 8° to approximately 10°).

In order to suppress the light emitted from the prism 318 from spreading in an optical axis direction, the inclined surface of the prism 31e may be formed as, for example, a curved surface whose center is an axis orthogonal to the optical axis and that is convex outward. In order to suppress the light emitted from the prism 318 from spreading in a circumferential direction around the optical axis, the other side (surface) on the distal end side of the prism 318 may be formed as, for example, a curved surface whose center is an axis parallel to the optical axis of light propagating through the optical fiber 310 and that is convex outward.

The above-described sheath 232 and optical probe 300 are provided in a state where the optical probe 300 is inserted into the sheath 232. At a time of use, the optical fiber 310 of the optical probe 300 is coupled to the rotation unit 238 with the connector 241 interposed therebetween, and the proximal end part of the sheath 232 is fixed to the base 226 by the retainer 233.

Therefore, the linear motion unit 228 and the optical probe 300 move forward and backward with respect to the base 226 based on driving of the linear motion motor 230. On the other hand, the sheath 232 is held by the base 226. Therefore, the optical probe 300 moves forward and backward in the sheath 232 based on driving of the linear motion motor 230. Furthermore, the rotation unit 238 rotates about the optical axis based on driving of the rotation motor 240. At this time, the optical probe 300 is coupled to the rotation unit 238 with the connector 241 interposed therebetween, and therefore rotates together with the rotation unit 238. Accordingly, the light sent from the first optical circulator 214 to the imaging unit 220 is incident on the optical fiber 310 through the proximal end side collimation lens 234 and the distal end side collimation lens 236, and is then emitted in the radial direction from the optical fiber 310 through the optical part 312, and this emission light is scanned at a constant speed in the circumferential direction whose center is the optical axis.

Sizes of the sheath 232 and the optical probe 300 accommodated in the sheath 232 are appropriately determined according to a size of a biological tubular element to be imaged. An inner diameter of the sheath 232 and an outer diameter of the optical probe 300 accommodated therein are determined to be, for example, approximately 50 μm larger than a maximum outer diameter of the glass rod 314, the grin lens 316, the prism 318, and a metal pipe (not illustrated) that holds these optical elements such that the optical probe 300 stably rotates in the sheath 232. In a case where, for example, the maximum outer diameter of the glass rod 314, the grin lens 316, the prism 318, and the metal pipe holding these optical elements is approximately 200 to 500 μm, the inner diameter of the sheath 232 is approximately 250 to 550 μm.

[Optical Distance Adjustment Unit]

The optical distance adjustment unit 222 includes a collimation lens 242 and a reference mirror 244. The collimation lens 242 is immovably fixed. The reference mirror 244 includes on the optical axis of the collimation lens 242 a reflection surface (mirror surface) that is vertical to the optical axis. The reference mirror 244 is supported by the linear motion unit 246. The linear motion unit 246 is movable along the optical axis of the collimation lens 242. The linear motion unit 246 is also coupled to the linear motion motor 248, and is configured to move forward and backward toward the collimation lens 242 based on driving of the linear motion motor 248, and thereby adjust an optical distance (optical distance) of reference light.

[Detection Unit]

The detection unit 224 is an optical part that receives light sent from the second optical coupler 218 and photoelectrically converts the light, and, more particularly, is a dual balanced detector that includes two light input units. The dual balanced detector includes two photodiodes that detect light (interference light) sent from the second optical coupler 218, and these two photodiodes are respectively coupled to distal ends of two optical fibers that make up the second optical coupler 218. The detection unit 224 is also configured to convert the light beams input from the two optical fibers into electric signals, then make direct current components included in the electric signals cancel each other, and thereby extract only the electric signals that are based on the interference light.

[Signal Processing Unit]

The signal processing unit 400 includes a control unit 410, an image adjustment unit 412, an analog-digital (A/D) conversion unit 414, a Fourier transform unit 416, an image processing unit (artifact deletion unit) 418, and an image display unit (monitor) 420. In the drawing, the image adjustment unit 412, the A/D conversion unit 414, the Fourier transform unit 416, and the image processing unit 418 indicate functional blocks, and do not need to have physical components, and may be part of a program that is installed in a storage unit of the control unit 410 described later.

[Control Unit]

Although not illustrated, the control unit 410 includes a controlling unit, an arithmetic operation unit, and a storage unit. The storage unit can temporarily store a program that is necessary to execute processing to be described later, and various items of data (e.g., image data) generated in a process of the processing to be described later. The arithmetic operation unit executes an arithmetic operation that needs to be executed in the process of the processing to be described later according to the program stored in the storage unit.

Although not illustrated, the control unit 410 is communicably connected with various devices (the wavelength swept light source 210, the optical probe rotation motor 240, the optical probe linear motion motor 230, and the reference mirror linear motion motor 249) included in the optical unit 200, and is configured to individually drive and control these devices according to the program of the storage unit. The control unit 410 is also communicably connected with the image adjustment unit 412, the analog-digital (A/D) conversion unit 414, the Fourier transform unit 416, the image processing unit (artifact deletion unit) 418, and the image display unit (monitor) 420, and is configured to exchange signals with these components.

Although not illustrated, the control unit 410 is connected to the input unit, and is configured to execute processing to be described below based on a signal input from the input unit. The input unit may be any of a keyboard, a pointing device, a touch screen, a mouse, a joystick, a trackball, a scanner, an OCR, an OMR, an audio input device, a tablet, and the like.

[Image Adjustment Unit]

The image adjustment unit 412 moves the reference mirror 244 by driving the linear motion motor 248 of the optical distance adjustment unit 222, and adjusts the optical distance of the reference light. In the embodiment, in an initial state, the image adjustment unit 412 sets the optical distance that the light emitted from the light source 210 travels until the light is reflected by the reference mirror 244 and reaches the detection unit 224 equally to an optical distance obtained by calculating a sum of the optical distance from the light source 210 to the prism inclined surface 320 and the optical distance from the prism inclined surface 320 to the detection unit 224.

A position of the reference mirror 244 in the initial state will be referred to as a "reference position" below. Therefore, when, for example, the reference mirror 244 is moved toward the collimation lens 242, a point (referred to as a "post-movement corresponding point 330" below) on an optical path of the reflected light corresponding to the position of the reference mirror 244 after the movement moves to a front side of the inclined surface 320 of the prism 318 (see FIG. 2). As a result, as will be described later, when the reference mirror 244 is moved toward the collimation lens 242, while distances from the post-movement corresponding point 330 on the optical path of the reflected light to the sheath 232 and a biological tubular element 500 become long, distances from the post-movement corresponding point 330 to bonding surfaces of the optical elements (bonding surfaces of the glass rod 314, the grin lens 316, and the prism 318) become short.

[A/D Conversion Unit]

The A/D conversion unit 414 converts an analog signal (an electric signal based on interference light) output from the detection unit 224 into a digital signal.

[Fourier Transform Unit]

The Fourier transform unit 416 performs Fourier transform (e.g., fast Fourier transform or discrete Fourier transform) on the digital signal output from the A/D conversion unit 414, and obtain an intensity (power spectrum) of the interference light with respect to the difference (optical distance difference) between the optical distance of the reflected light and the optical distance of the reference light.

Figure 3A:
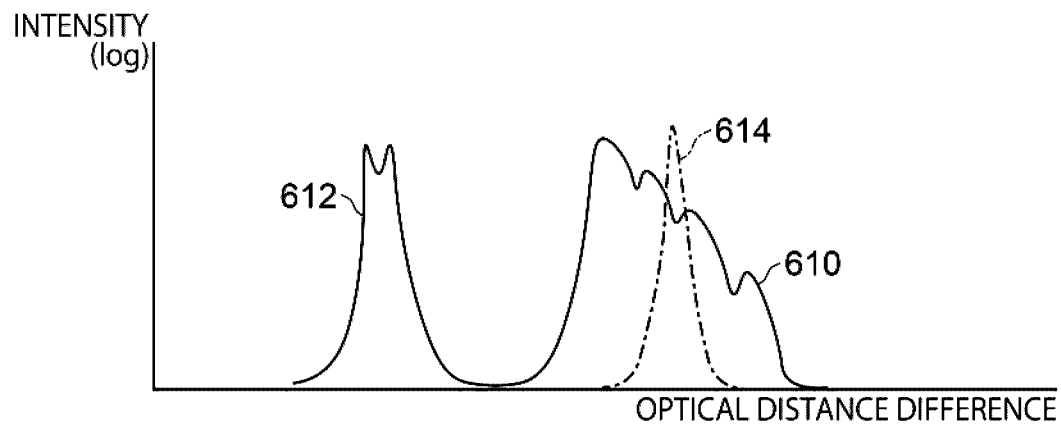
FIG. 3A illustrates an intensity distribution of an OCT signal obtained by the optical tomographic imaging device illustrated in FIG. 1.

FIG. 3A illustrates a relationship between an optical distance difference and an intensity obtained when the optical probe 300 covered with the sheath 232 is inserted into the biological tubular element 500 (e.g., blood vessel) as illustrated in FIG. 2. In this FIG. 3A, a horizontal axis indicates the optical distance difference on a linear scale, a vertical axis indicates the intensity on a logarithmic scale, an intensity distribution denoted by reference numeral 610 corresponds to interference light of reflected light from the biological tubular element 500 and reference light, and an intensity distribution denoted by reference numeral 612 corresponds to interference light of reflected light from the sheath 232 and reference light. In FIG. 3A, an intensity distribution denoted by reference numeral 614 corresponds to interference light (above-described artifact 700A) of light reflected or scattered on or near the bonding surfaces of the optical elements (bonding surfaces of the glass rod 314, the grin lens 316, and the prism 318) that make up the optical probe 300 and reference light. Although the intensity distribution 610 of the biological tubular element 500 and the intensity distribution 614 of the artifact 700A are separately displayed in FIG. 3A for ease of understanding, an actually obtained power spectrum appears in a form obtained by synthesizing the two intensity distributions 610 and 614. Furthermore, in FIG. 3A, the intensity distribution 610 of the biological tubular element 500 and the intensity distribution 614 of the artifact 700A appear (overlap) in the same optical distance difference area because the optical distance from the prism inclined surface 320 (reference surface) to the biological tubular element 500 and the optical distance from the prism inclined surface 320 to the bonding surfaces of the optical elements (the bonding surfaces of the glass rod 314, the grin lens 316, and the prism 318) are substantially equal.

[Image Processing Unit]

The image processing unit 418 receives a power spectrum including the spectral components 610 and 612 of the biological tubular element 500 and the sheath 232 and the spectral component 614 of an artifact 700 from the Fourier transform unit 416, and outputs image information per rotation angle of the optical probe 300 according to the intensity distributions 610, 612, and 614 of the biological tubular element 500, the sheath 232, and the artifact 700 in the power spectrum.

The image processing unit 418 also deletes an image portion (more specifically, the artifact) of an instructed area in the captured image based on an instruction from the control unit 410 as described in detail later.

[Image Display Unit]

The image display unit 420 is a general monitor.

Figure 4A:
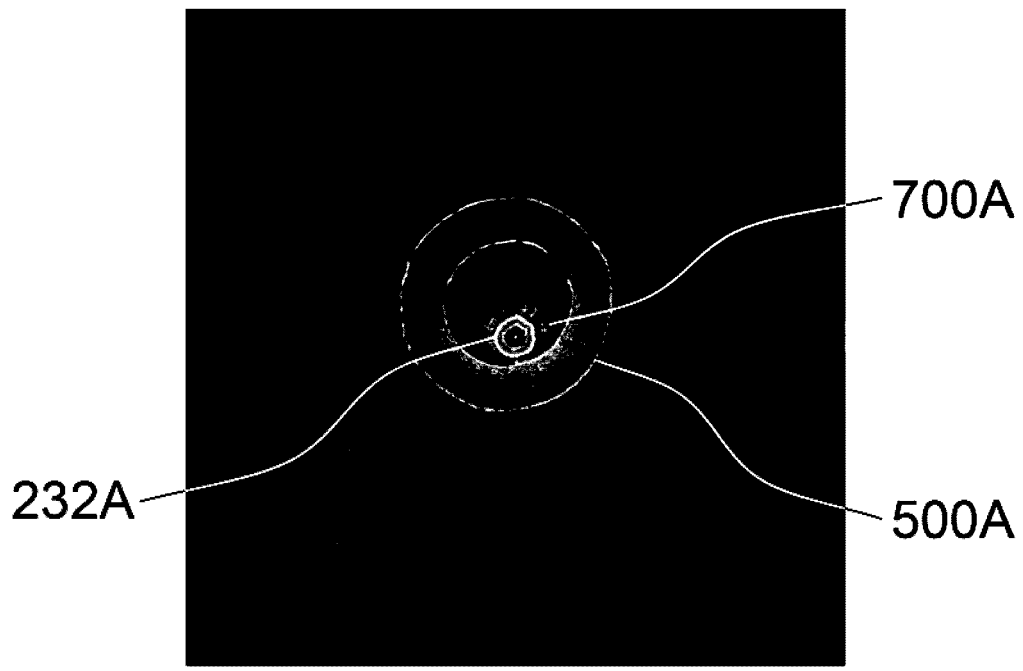
FIG. 4A is a view illustrating a tomographic image of a biological tubular element including an artifact caused by an optical part.

For reference, FIG. 4A illustrates a captured image obtained when the optical probe 300 covered with the sheath 232 is inserted into the biological tubular element 500 (e.g., blood vessel) as illustrated in FIG. 2. In FIG. 4A, an image portion denoted by reference numeral 500A corresponds to the biological tubular element 500, an image portion denoted by reference numeral 232A corresponds to the sheath 232, and an image portion (referred to as an "artifact" below) denoted by reference numeral 700A corresponds to light reflected or scattered on or near the bonding surfaces of the optical elements.

[Optical Tomographic Imaging]

Optical tomographic imaging that uses the above-described SS-OCT 100 will be described.

The optical probe 300 is inserted together with the sheath 232 into an imaging site of a biological tubular element (a gastrointestinal tract, a pancreaticobiliary duct, a fallopian tube, a urethra, a trachea, a blood vessel, or a lymph duct) of a human or an animal. When, for example, a cross section of a blood vessel of a human is imaged, a guide wire is inserted from a basilic vein of the upper arm, and then the optical probe 300 and the sheath 232 are inserted to a target site along a guide wire.

When the optical probe 300 is moved, an operator inputs a necessary signal to the control unit 410 through an unillustrated input unit. The control unit 410 that has received this signal drives the linear motion motor 230 of the biological tubular element imaging unit 220 to move the linear motion unit 226 forward or backward.

Next, the control unit 410 drives the rotation motor 240 of the biological tubular element imaging unit 220 based on a driving start signal from the unillustrated input unit to rotate the optical probe 300 at a speed of, for example, 180 rps.

Next, the control unit 410 drives the wavelength swept light source 210 to emit light of a predetermined wavelength. The light emitted from the wavelength swept light source 210 is split into first light traveling to the biological tubular element imaging unit 220, and second light traveling to the optical distance adjustment unit 222 in the first optical coupler 212.

The split first light is sent to the biological tubular element imaging unit 220 via the first optical circulator 214, and is incident on the optical fiber 310 of the optical probe 300 through the proximal end side collimation lens 234 and the distal end side collimation lens 236. The light incident on the optical fiber 310 passes through the core of the optical fiber 310, then reaches the inclined surface 320 (reference surface) of the prism 318 via the glass rod 314 and the grin lens 316, and is reflected by the inclined surface 320. The light reflected by the inclined surface 320 of the prism 318 is emitted in the radial direction from a prism outer circumferential surface 322. The light emitted from the prism 318 is transmitted through the sheath 232 and radiated on an entire circumference of an inner wall of the biological tubular element 500 while moving in the circumferential direction based on rotation of the optical probe 300. The light reflected by the biological tubular element 500 and biological tissues around the biological tubular element 500 enters the prism 318 through the outer circumferential surface 322 of the prism 318, is reflected by the inclined surface 320, and then is sent to the first optical circulator 214 through the grin lens 316, the glass rod 314, the optical fiber 310, the distal end side collimation lens 236, and the proximal end side collimation lens 234. The first optical circulator 214 sends the reflected light from the biological tubular element imaging unit 220 toward the second optical coupler 218.

The reflected light sent to the first optical circulator 214 includes the reflected light from the biological tubular element 500 and the sheath 232, and, in addition, unnecessary reflected light and scattered light from the bonding surfaces of the glass rod 314, the grin lens 316, and the prism 318 (see FIGS. 3A and 4A).

The second light split by the first optical coupler 212 is sent from the second optical circulator 216 to the optical distance adjustment unit 222, emitted from the collimation lens 242, then reflected by the reference mirror 244 facing this collimation lens 242, and sent again to the second optical circulator 216 through the collimation lens 242. The second optical circulator 216 sends the reference light from the optical distance adjustment unit 222 toward the second optical coupler 218.

The reflected light sent to the second optical coupler 218 and the reference light are synthesized to obtain interference light. The interference light is split into two light beams, and each light beam is incident on the detection unit 224.

The detection unit 224 photoelectrically converts the interference light to generate an analog signal corresponding to the interference light. The generated analog signal is sent to the A/D conversion unit 414, and converted into a digital signal.

FIG. 4A illustrates an image (an unprocessed image including an artifact) created based on the digital signal. As illustrated in FIG. 4A, the unprocessed image includes the image portion 500A of the biological tubular element 500, the image portion 232A of the sheath 232, and, in addition, and, in addition, the image portion (artifact) 700A of light reflected or scattered on or near the bonding surfaces of the optical elements of the optical probe 300. In the embodiment, the distance from the prism inclined surface (reference surface) 320 to the biological tubular element 500 and the distance from the prism inclined surface (reference surface) 320 to the bonding surfaces of the optical elements (the bonding surfaces of the glass rod 314, the grin lens 316, and the prism 318) are set substantially equally. Hence, the artifact 700A overlaps the image portion 500A of the biological tubular element 500 of most interest, which makes the image of the image portion 500A unclear.

As described above, the digital signal including information of the artifact 700A is sent to the Fourier transform unit 416. The Fourier transform unit 416 performs Fourier transform (fast Fourier transform or discrete Fourier transform) on the digital signal. As a result, as illustrated in FIG. 3A, an intensity distribution (power spectrum) of the interference light corresponding to the optical distance difference between the optical distance of the reference light and the optical distance of the reflected light is obtained. As described above, the distance from the prism inclined surface (reference surface) 320 to the biological tubular element 500 and the distance from the prism inclined surface (reference surface) 320 to the bonding surfaces of the optical elements are substantially equal, and therefore the intensity distribution 614 of the artifact 700A appears in substantially the same optical distance difference area as that of the intensity distribution 610 of the biological tubular element 500. Therefore, as illustrated in FIG. 4A, the artifact 700A appears overlapping the image 500A of the biological tubular element 500.

Figure 3B:
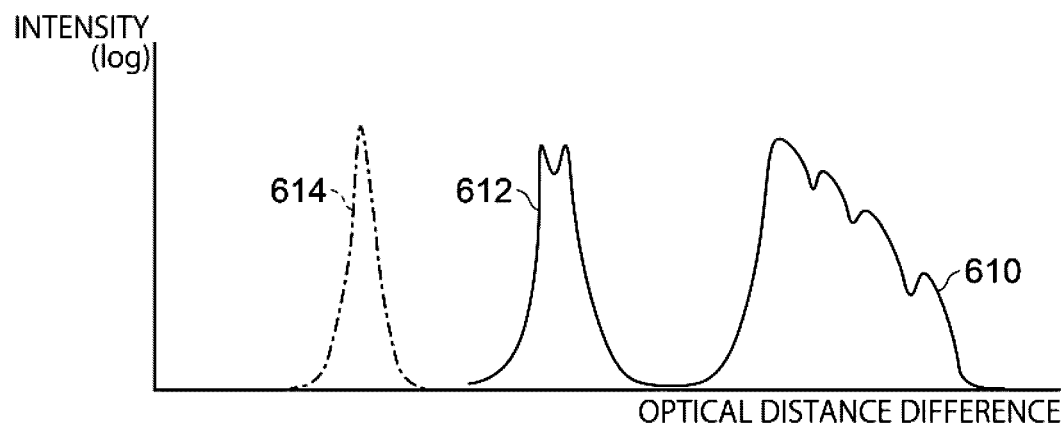
FIG. 3B illustrates an intensity distribution of an OCT signal obtained by the optical tomographic imaging device illustrated in FIG. 1.
Figure 3C:
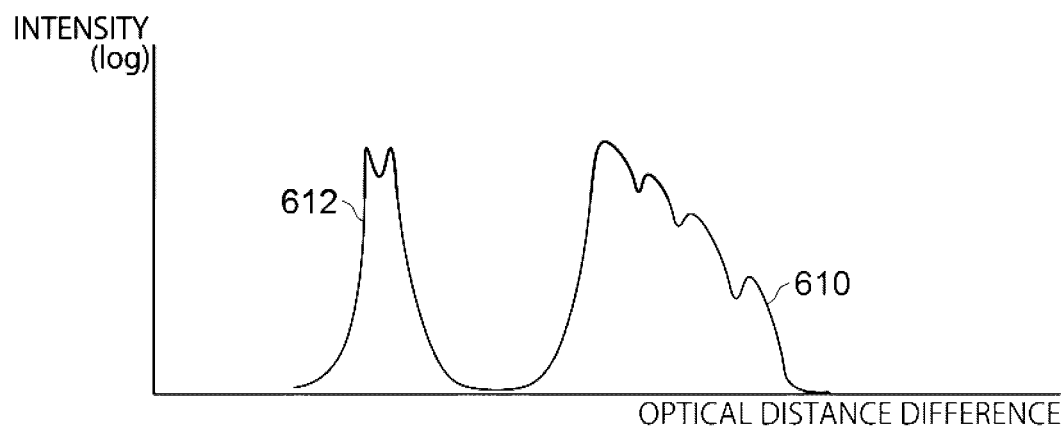
FIG. 3C illustrates an intensity distribution of an OCT signal obtained by the optical tomographic imaging device illustrated in FIG. 1.
Figure 4B:
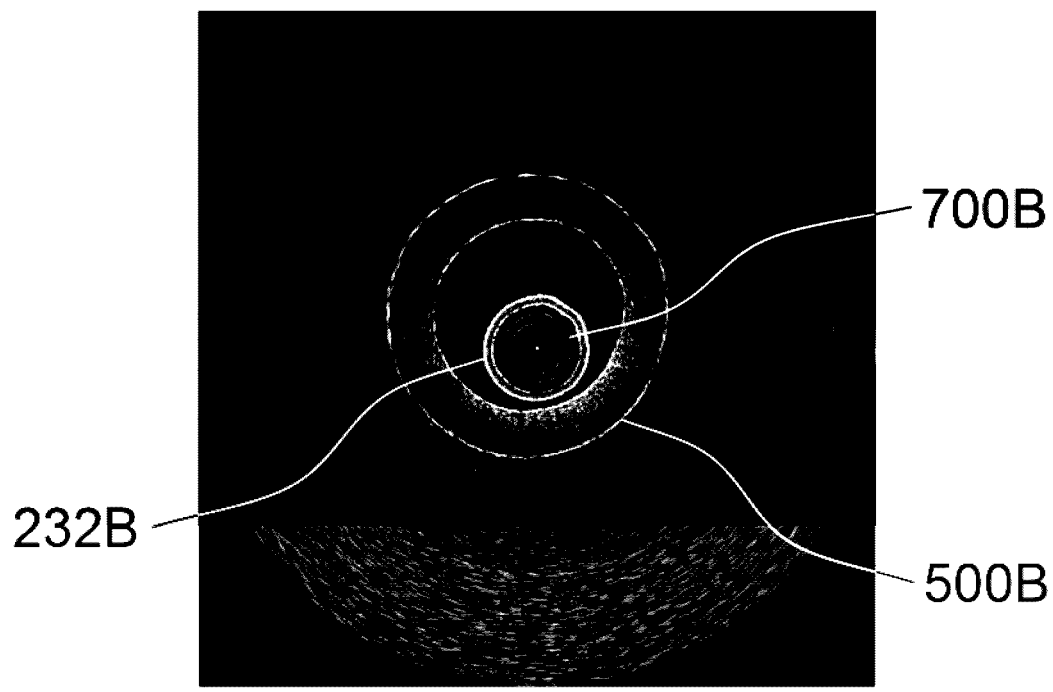
FIG. 4B is a view illustrating a state where the artifact is made small in the tomographic image of the biological tubular element.

In order to remove the artifact 700A and make the image 500A of the biological tubular element 500 clear, the control unit 410 drives the linear motion motor 248 of the optical distance adjustment unit 222 via the image adjustment unit 412 to bring the reference mirror 244 close to the collimation lens 242. Thus, the optical distance that the reference light reflected by the reference mirror 244 travels until reaching the detection unit 224 becomes short. As a result, while the difference between the optical distance of the reflected light from the biological tubular element 500 and the sheath 232 and the optical distance of the reference light becomes great, the difference between the optical distance of the reflected light or the scattered light from the bonding surface of the optical part 312 in the optical probe 300 and the optical distance of the reference light becomes a little. Hence, as illustrated in FIG. 4B, while an image portion 500B of the biological tubular element 500 and an image portion 232B of the sheath 232 are enlarged, an image portion 700B of the artifact is reduced, and the image portion 700B of the artifact is fitted to an inside of the image portion 232B of the sheath 232. Therefore, as illustrated in FIG. 3B, in the power spectrum obtained by performing Fourier transform on the interference light after the optical distance adjustment, the intensity distributions 610 and 612 of the biological tubular element 500 and the sheath 232 move to a right side in FIG. 3B, and the intensity distribution 614 of the artifact caused by the light reflected or scattered on or near the bonding surface of the optical element moves to a left side in FIG. 3B, such that the intensity distributions 610 and 612 and the intensity distribution 614 are separated so as not to overlap each other.

The distance that the reference mirror 244 moves will be described. In the SS-OCT 100, a size (an inner diameter and an outer diameter) of the sheath 232 and sizes (lengths in the optical axis direction) of the optical elements (the glass rod 314, the grin lens 316, and the prism 318) of the optical probe 300 are determined according to models of the sheath 232 and the probe 300, and information of these sizes is stored in the storage unit of the control unit 410. Therefore, according to models of the sheath 232 and the probe 300, the control unit 410 determines a movement distance of the reference mirror 244 such that the optical distance to the sheath 232 from the post-movement corresponding point 330 (FIG. 2) on the optical path of the reflected light corresponding to the position of the reference mirror 244 after movement is longer than the optical distance from the post-movement corresponding point 330 to the bonding surfaces of the optical elements such as the bonding surfaces of the grin lens 316 and the prism 318. This movement distance may be stored according to the models of the sheath 232 and the probe 300, and the control unit 410 may move the reference mirror 244 based on stored values.

Next, the control unit 410 activates the image processing unit 419, and deletes the image portion 700B of the reduced artifact from the image illustrated in FIG. 4B. More specifically, the control unit 410 deletes the image data inside the annular image portion 232B of the sheath 232 (the image portion 700B corresponding to the artifact), that is, image data within an optical distance difference range including the intensity distribution 614 in FIG. 3B. The optical distance difference range corresponding to the image data that needs to be deleted corresponds to the movement distance of the above-described reference mirror 244, is determined in advance according to the models of the sheath 232 and the probe 300 together with the movement distance, and is stored in the storage unit.

Figure 4C:
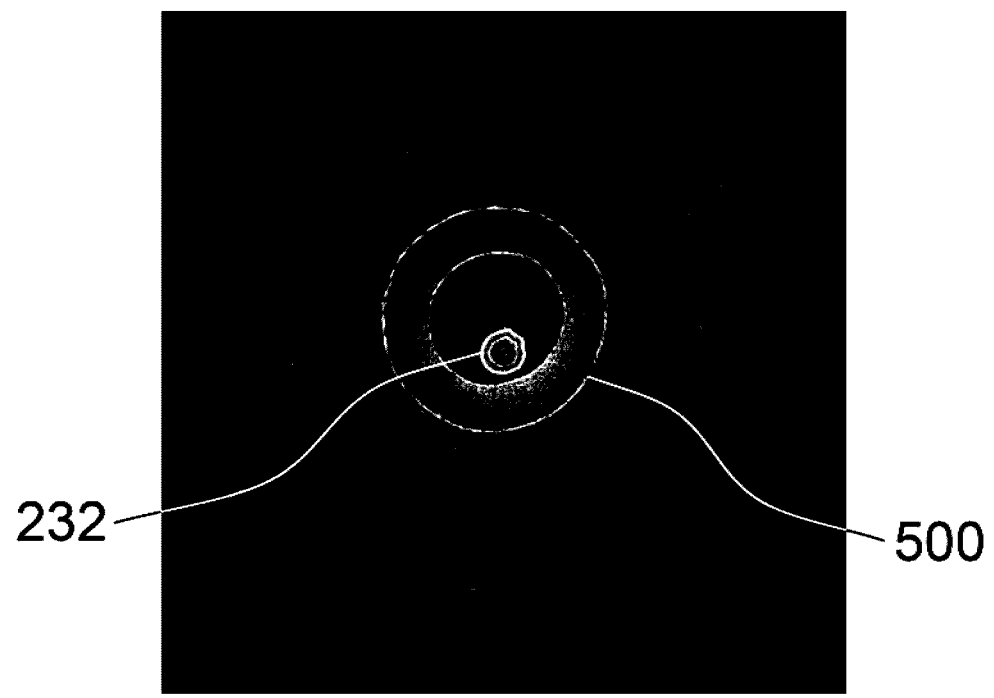
FIG. 4C is a view illustrating a tomographic image of the biological tubular element obtained by removing the artifact from FIG. 4A.

Subsequently, the control unit 420 resets the enlarged image (see FIG. 4B) from which the image data of the artifact has been deleted to a magnification of the image before enlargement illustrated in FIG. 4A. FIG. 4C illustrates an image whose magnification has been reset, and that includes no artifact.

Finally, the control unit 410 displays the image illustrated in FIG. 4C on the display unit 420. As described above, the image portion of the artifact is removed from the image displayed on the display unit 420. Consequently, it is possible to obtain a clear biological tubular element tomographic image without the artifact. As a result, reliability of the image to be obtained increases, and reliability of diagnosis that uses this image increases.

Note that, although FIG. 4A illustrates the image including the artifact, and FIG. 4B illustrates the image enlarged from the image of FIG. 4A in the above description to facilitate understanding of the invention, an actual device does not display these images on the display unit 420. Naturally, the images in FIGS. 4A and 4B may be displayed on the display unit 420 to indicate presence of the artifact.

Other Embodiment

Although the control unit 410 activates the image processing unit 418 to delete the reduced image portion 700B of the artifact from the enlarged image illustrated in FIG. 4B in the above-described embodiment, this reduced image portion 700B of the artifact may not be deleted. In this case, even when the control unit 410 resets the enlarged image illustrated in FIG. 4B to the magnification of the image before the enlargement illustrated in FIG. 4A, the image portion 700B of the artifact remains fitted inside the image portion 232B of the sheath 232, and therefore the image portion 500B of the biological tubular element 500 and the image portion 700B of the artifact do not overlap. Consequently, even if the reduced image portion 700B of the artifact is not deleted, reliability of an image to be obtained increases, and reliability of diagnosis that uses this image increases.

Furthermore, to continuously obtain images, the control unit 410 may perform a pull-back operation of moving the linear motion unit 229 backward while rotating the optical probe 300. In this case, after displaying the image illustrated in FIG. 4C on the display unit 420, the control unit 410 operates the biological tubular element imaging unit 220 to image the biological tubular element 500 while moving the optical probe 300 backward along the sheath 232 by the poll-back operation. At this time, the position of the reference mirror 244 has already been adjusted, and therefore while the image portion of the biological tubular element 500 and the image portion of the sheath 232 are enlarged as described above, the image portion of the artifact is reduced and fitted inside the image portion of the sheath 232. After imaging by this pull-back operation, the control unit 410 resets the enlarged image after the image data of the artifact is deleted or the enlarged image in which the image portion of the artifact remains fitted inside the image portion of the sheath 232 to the magnification of the image before enlargement by the same method as that described above, and then displays the image reset to the magnification of the image before enlargement on the display unit 420. As described above, the control unit 410 can continuously obtain images by repeating imaging by the pull-back operation, the process of resetting the enlarged image to the magnification of the image before enlargement, and the process of displaying on the display unit 420 the image reset to the magnification of the image before enlargement.

Although the optical probe 300 includes the glass rod 314, the grin lens 316, and the prism 318 in the above-described embodiments, the optical parts making up the optical probe 300 are not limited to these. An optical element may be formed in place of a prism by, for example, obliquely machining a distal end of a core of an optical fiber, and light may be radiated in the radial direction from an inclined surface of this distal end. Furthermore, the optical probe may include an optical fiber and a glass rod or a plastic rod including an inclined distal end surface. Alternatively, the optical probe may include an optical fiber and a ball-type lens including an inclined distal end and surface.

Although the optical distance of the reference light is set using the inclined surface 320 of the prism 318 as the reference surface in the above-described embodiments, the outer circumferential surface 322 of the prism 318 may be used as the reference surface.

Furthermore, the image processing unit 418 may include a change amount detection unit (not illustrated) that detects an amount of change in an optical distance difference between the optical distance of reference light and an optical distance of reflected light when obtaining an image. This change amount detection unit automatically detects the amount of change in the optical distance difference between the optical distance of the reference light and the optical distance of the reflected light caused by, for example, expansion and contraction of the optical fiber 310 during imaging by the SS-OCT 100, and sends an instruction that is based on the amount of change to the image adjustment unit 412 through the control unit 410. The image adjustment unit 412 moves the reference mirror 244 based on above the instruction by driving the linear motion motor 240 of the optical distance adjustment unit 222, and automatically adjusts the optical distance of the reference light. Consequently, the optical distance difference between the optical distance of the reference light and the optical distance of the reflected light is automatically maintained. Consequently, it is possible to reliably delete an artifact from a tomographic image without changing the amount of change in the optical distance difference between the optical distance of the reference light and the optical distance of the reflected light during imaging.

As described above, a method for operating an optical tomographic imaging apparatus is provided, the optical tomographic imaging apparatus comprising:

a light source;

a splitter that splits light emitted from the light source into first light and second light;

a translucent tube that is inserted into a biological tubular element;

an imaging unit that includes an optical fiber having a proximal end optically coupled to the splitter, and an optical part provided at a distal end of the optical fiber, and that emits the first light guided by the optical fiber from the optical part toward an inner wall of the biological tubular element through the tube, and obtain reflected light of the first light returning from the biological tubular element via the tube, from the optical part through the optical fiber;

an optical distance adjustment unit that includes a movable reference mirror, and is capable of obtaining reference light by reflecting the second light on the reference mirror, and adjusting an optical distance of the second light by moving the reference mirror;

an interference unit that causes the reflected light and the reference light to interfere with each other, and obtains interference light;

a detection unit that detects the interference light of the reflected light and the reference light;

a conversion unit that converts the interference light detected by the detection unit into an electrical signal;

a Fourier transform unit that performs Fourier transform on the electrical signal obtained by the conversion unit, and obtains a light intensity distribution with respect to an optical distance difference between an optical distance of the reflected light and an optical distance of the reference light;

an image processing unit that deletes an image portion of an artifact caused by the optical part from an image imaged by the image imaging unit, and obtains an image without the artifact;

an image display unit; and a control unit that controls the imaging unit, the optical distance adjustment unit, the image processing unit, and the image display unit, the method comprising executing, by the control unit:

(a) an initial setting step of controlling the optical distance adjustment unit to set an optical distance of the reference light substantially equally to an optical distance of the reflected light, the optical distance of the reference light being an optical distance that light emitted from the light source travels until reaching the detection unit after being reflected by the reference mirror, and the optical distance of the reflected light being an optical distance obtained by adding a first optical distance from the light source to a distal end of the optical part and a second optical distance from the distal end of the optical part to the detection unit;

(b) an imaging step of, after the initial setting step, operating the imaging unit to image the biological tubular element;

(c) a reference mirror adjustment step of, after the imaging step, controlling the optical distance adjustment unit to move the reference mirror to make the optical distance of the reference light shorter than the optical distance of the reflected light, thereby enlarge the image portion of reflected light from the biological tubular element and the image portion of reflected light from the tube while reducing an image portion of an artifact caused by the reflected light from the optical part, and fitting the image portion of the artifact to an inside of the image portion of the reflected light from the tube;

(d) a magnification adjustment step of, after the reference mirror adjustment step, controlling the image processing unit to reset the image portion of the reflected light from the biological tabular element and the image portion of the reflected light from the tube to a state before the enlargement; and (e) a display step of, after the magnification adjustment step, causing the image display unit to display the image portion of the reflected light from the biological tubular element and the image portion of the reflected light from the tube reset to the state before the enlargement.

According to the method according to embodiments of the present invention, an artifact caused by an optical part does not overlap a tomographic image of the biological tubular element. Consequently, it is possible to appropriately perform diagnosis that uses tomographic images.

It is to be noted that the various embodiments described above can be appreciated individually within each embodiment, but the embodiments can be combined together. It is also to be rioted that the various features in different embodiments can be appreciated individually by its own, but the features in different embodiments can be combined.

The invention claimed is:

1. A method for operating an optical tomographic imaging apparatus, the optical tomographic imaging apparatus comprising:
a light source;
a splitter that splits light emitted from the light source into first light and second light;
a translucent tube that is inserted into a biological tubular element;
an imaging unit that includes an optical fiber having a proximal end optically coupled to the splitter, and an optical part provided at a distal end of the optical fiber, and that emits the first light guided by the optical fiber from the optical part toward an inner wall of the biological tubular element through the translucent tube, and obtain reflected light of the first light returning from the biological tubular element via the translucent tube, from the optical part through the optical fiber;
an optical distance adjustment unit that includes a movable reference mirror, and is capable of obtaining reference light by reflecting the second light on the reference mirror, and adjusting an optical distance of the second light by moving the reference mirror;
an optical coupler that causes the reflected light and the reference light to interfere with each other, and obtains interference light;
a detector that detects the interference light of the reflected light and the reference light and photoelectrically converts the interference light to generate an analog signal corresponding to the interference light;
a converter that receives the analog signal from the detector and converts the analog signal into a digital signal;
a Fourier transform unit that performs Fourier transform on the digital signal obtained by the converter to obtain a light intensity distribution chart with respect to an optical distance difference between an optical distance of the reflected light and an optical distance of the reference light;
an image display;
an image processor that deletes data corresponding to an intensity corresponding to the artifact from the digital data Fourier-transformed by Fourier transform unit, so that an image without the artifact is displayed on the image display; and
a controller, wherein the imaging unit, the optical distance adjustment unit, the image processor, and the image display are configured to be controlled by the controller,
the method comprising executing, by the controller:
(a) an initial setting step of controlling the optical distance adjustment unit to set an optical distance of the reference light substantially equally to an optical distance of the reflected light, the optical distance of the reference light being an optical distance that light emitted from the light source travels until reaching the detector after being reflected by the reference mirror, and the optical distance of the reflected light being an optical distance obtained by adding a first optical distance from the light source to a distal end of the optical part and a second optical distance from the distal end of the optical part to the detector;
(b) an imaging step of, after the initial setting step, operating the imaging unit to image the biological tubular element though the translucent tube by detecting the reflected light by the detector;
(c) a reference mirror adjustment step of, after the imaging step, controlling the optical distance adjustment unit to move the reference mirror to make the optical distance of the reference light shorter than the optical distance of the reflected light, so that i) the image portion of reflected light from the biological tubular element and the image portion of reflected light from the translucent tube are enlarged and ii) an image portion of an artifact caused by the reflected light from the optical part is reduced, whereby fitting the image portion of the artifact within an inside of the image portion of the reflected light from the translucent tube;
(d) a magnification adjustment step of, after the reference mirror adjustment step, controlling the image processor to delete the data corresponding to the intensity corresponding to the artifact, and then, decrease size of the image portion of the reflected light from the biological tubular element and the image portion of the reflected light from the translucent tube to size before the enlargement; and
(e) a display step of, after the magnification adjustment step, causing the image display to display the image portion of the reflected light from the biological tubular element and the image portion of the reflected light from the translucent tube.

2. The method according to claim 1, further comprising an artifact deletion step of controlling the image processor to delete the reduced image portion of the artifact is executed after the reference mirror adjustment step and before the magnification adjustment step.

3. The method according to claim 1, wherein
the optical tomographic imaging apparatus comprises a linear motion unit driven by a motor that moves the optical part of the imaging unit along the translucent tube,
the method further comprises:
a pull-back imaging step of operating the imaging unit to image the biological tubular element while operating the linear motion unit to move the optical part along the translucent tube is executed after the display step,
the magnification adjustment step and the display step are executed after the pull-back imaging step, and
the pull-back imaging step, the magnification adjustment step, and the display step are repeated in order.

4. The method according to claim 1, wherein
the optical part includes a prism,
the prism is a right angle prism that includes one end connected with a first side and a second side connected via a right angle, and one oblique side connecting another end of the first side and another end of the second side,
the first side of the right angle prism is optically coupled to a distal end of the optical fiber,
the light emitted from the distal end of the optical fiber is reflected by the oblique side and then emitted through the second side, and light reflected by the biological tubular element is incident on the right angle prism from the second side, reflected by the oblique side, and then incident on the optical fiber through the first side.

5. The method according to claim 1, wherein the detector is a dual balanced detector.

6. The method according to claim 1, wherein the converter is an analog-digital conversion unit.

7. The method according to claim 1, wherein the Fourier transform unit is a computer program implemented on the controller.

8. The method according to claim 1, wherein the image processor is a computer program implemented on the controller.

9. The method according to claim 1, wherein the controller is a processor or a computer.

10. The method according to claim 1, wherein the optical distance adjustment unit includes a collimation lens, and
   in the reference mirror adjustment step (c), the optical distance adjustment unit is controlled to move the reference mirror toward the collimation lens to make the optical distance of the reference light shorter than the optical distance of the reflected light.

* * * * *